United States Patent
Kodama et al.

(10) Patent No.: US 8,529,688 B2
(45) Date of Patent: Sep. 10, 2013

(54) PHENOLIC COMPOUND AND RECORDING MATERIAL

(75) Inventors: Satoshi Kodama, Ichihara (JP); Shinichi Satoh, Tokyo (JP); Toshio Aihara, Ichihara (JP); Tadashi Kawakami, Ichihara (JP); Kazumi Jyujyo, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 17 days.

(21) Appl. No.: 13/138,301

(22) PCT Filed: Feb. 1, 2010

(86) PCT No.: PCT/JP2010/000573
§ 371 (c)(1),
(2), (4) Date: Jul. 29, 2011

(87) PCT Pub. No.: WO2010/089984
PCT Pub. Date: Aug. 12, 2010

(65) Prior Publication Data
US 2011/0308429 A1    Dec. 22, 2011

(30) Foreign Application Priority Data
Feb. 3, 2009   (JP) ................................. 2009-022193

(51) Int. Cl.
*C09D 7/12*    (2006.01)
*C07C 235/38*  (2006.01)

(52) U.S. Cl.
USPC ................. 106/287.25; 564/170; 564/182

(58) Field of Classification Search
None
See application file for complete search history.

(56) References Cited

U.S. PATENT DOCUMENTS 4,026,896 A * 5/1977 Harita et al. ............. 514/466
6,017,919 A   1/2000 Inaba et al.

FOREIGN PATENT DOCUMENTS

| | | |
|---|---|---|
| EP | 0 374 048 A1 | 6/1990 |
| JP | 50-135048 A | 10/1975 |
| JP | 51-001439 A | 1/1976 |
| JP | 60-097946 A | 5/1985 |
| JP | 05-058894 A | 3/1993 |
| JP | 2003-305959 A | 10/2003 |
| JP | 2005-518371 A | 6/2005 |
| WO | WO 97/29027 A1 | 8/1997 |
| WO | WO 03/049702 A2 | 6/2003 |

OTHER PUBLICATIONS

International Search Report mailed Mar. 23, 2010, in PCT/JP2010/000573, 2 pages.
Reihmann et al., "Enzymatically catalyzed synthesis of photocrosslinkable oligophenols," Macromol. Chem. Phys., 2000, 201:1593-1597.

* cited by examiner

*Primary Examiner* — Yun Qian
(74) *Attorney, Agent, or Firm* — Foley & Lardner LLP

(57) ABSTRACT

Provided is a recording material with a superior storage property for the background and image, particularly with a remarkable superiority in any of light resistance of the background, and light, moisture and heat resistance of the image. The recording material contains a phenolic compound represented by formula (I) [wherein $R^1$-$R^3$ each independently represent a hydrogen atom or $C_1$-$C_4$ alkyl group; $R^5$ represents a hydrogen atom, $C_1$-$C_4$ alkyl group or $C_1$-$C_4$ alkoxy group, with the proviso that when $R^5$ is a hydrogen atom, $R^4$ is a $C_1$-$C_4$ alkyl group, when $R^5$ is a $C_1$-$C_4$ alkyl group, $R^4$ is a hydrogen atom, and when $R^5$ is a $C_1$-$C_4$ alkoxy group, $R^4$ is a $C_1$-$C_4$ alkoxy group].

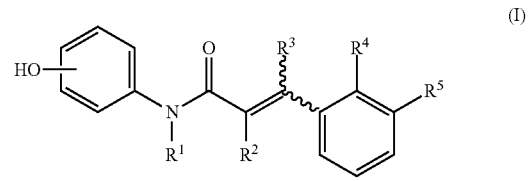

(I)

2 Claims, No Drawings

PHENOLIC COMPOUND AND RECORDING MATERIAL

TECHNICAL FIELD

The present invention relates to a phenolic compound, and a recording material containing the phenolic compound and having a superior storage property for the background and the image. The present application claims priority to Japanese Patent Application No. 2009-22193 filed on Feb. 3, 2009, the content of which is hereby incorporated by reference.

BACKGROUND ART

Recording materials that utilize color formation resulted by reaction of a color-forming compound and a color-developing agent makes it possible to carry out recording in a short time with a relatively simple device without conducting cumbersome treatments such as developing/fixing. Such recording materials are thus widely used for thermal recording papers used for output recording such as for a facsimile and a printer, as well as for pressure sensitive copying papers used for the simultaneously copying multiple ledger sheets. As for these recording materials, those recording materials are desired in which color is formed swiftly, whiteness of the no color-forming part (hereinafter referred to as "background") is retained, and toughness of the colored image is high. Especially, recording materials with a superior light resistance of the background are awaited in view of the long-term storage stability. For this purpose, efforts have been made to develop color-forming compounds, color-developing agents, storage stabilizers, etc. In spite of such efforts, those recording materials that are sufficiently satisfactory with well balanced color-formation sensitivity, storage property for the background and the image, etc. have not yet been found.

Further, 2,4'-dihydroxydiphenylsulfone and 4-isopropoxy-4'-hydroxydiphenylsulfone have conventionally been known as a recording material with a superior background storage property, but the background light resistance thereof has not yet been satisfactory.

The present inventors have already proposed a recording material with a superior background light resistance comprising a cinnamic acid amide-based compound as a color-developing agent (see Patent Document 1), which, however, is not yet sufficiently satisfactory. Hence, practically usable recording materials have not yet been obtained.

[Patent Document 1] Japanese Unexamined Patent Application Publication No. 2003-305959

SUMMARY OF THE INVENTION

Object to be Solved by the Invention

The object of the present invention is to remedy the drawbacks of conventional recording materials as mentioned above, and to provide a recording material with a superior storage property for the background and the image, especially, a recording material which is remarkably superior in light resistance of the background as well as light, moisture and heat resistance of the image.

Means to Solve the Object

The present inventors have already found that a recording material which is superior in the background light resistance can be provided by using a cinnamic acid amide-based compound as a color-developing agent (Japanese Unexamined Patent Application Publication No. 2003-305959).

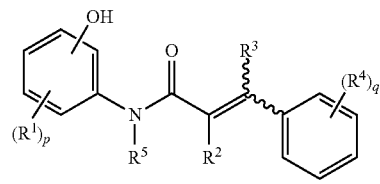

[wherein $R^1$ and $R^4$ each independently represent a hydrogen atom, hydroxy group, halogen atom, $C_1$-$C_6$ alkyl group or $C_1$-$C_6$ alkoxy group; p represents any integer of 0 to 4; q represents any integer of 0 to 5; when p or q is 2 or more, $R^1$s and $R^4$s may be the same or different; $R^2$ and $R^3$ each independently represent a hydrogen atom or $C_1$-$C_6$ alkyl group; and $R^5$ represents a hydrogen atom, $C_1$-$C_6$ alkyl group, optionally substituted phenyl group, and optionally substituted benzyl group]

The above recording material, however, has not yet reached a practical level and a higher light resistance is desired. The present inventors have further made a keen study of color-developing agent compounds to be used for such recording material and have found that a recording material with a remarkably superior light resistance of the background and a superior light resistance of the colored image is obtained by using as a color-developing agent a compound wherein a particular position is substituted by a particular substituent in the previously discovered cinnamic acid amide-based compound.

In addition, the present inventors have found that an unprecedented recording material having a remarkably superior moisture and heat resistance of the colored image and exerting a comprehensive superiority in both the background and the image can be provided. Thus, the present invention was completed.

The present invention thus relates to: (1) a phenolic compound represented by formula (I)

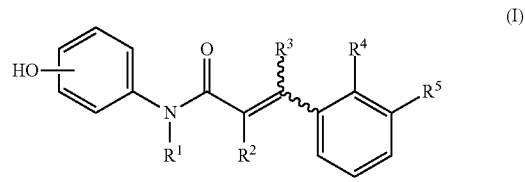

[wherein $R^1$-$R^3$ each independently represent a hydrogen atom or $C_1$-$C_4$ alkyl group; $R^5$ represents a hydrogen atom, $C_1$-$C_4$ alkyl group or $C_1$-$C_4$ alkoxy group, with the proviso that when $R^5$ is a hydrogen atom, $R^4$ is a $C_1$-$C_4$ alkyl group, when $R^5$ is a $C_1$-$C_4$ alkyl group, $R^4$ is a hydrogen atom, and when $R^5$ is a $C_1$-$C_4$ alkoxy group, $R^4$ is a $C_1$-$C_4$ alkoxy group]; (2) the phenolic compound according to (1), which is represented by formula (II)

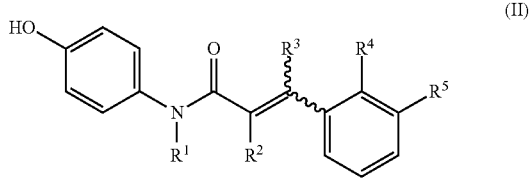

[wherein $R^1$-$R^3$ represent a hydrogen atom; $R^5$ represents a hydrogen atom, $C_1$-$C_4$ alkyl group or $C_1$-$C_4$ alkoxy group, with the proviso that when $R^5$ is a hydrogen atom, $R^4$ is a $C_1$-$C_4$ alkyl group, when $R^5$ is a $C_1$-$C_4$ alkyl group, $R^4$ is a hydrogen atom, and when $R^5$ is a $C_1$-$C_4$ alkoxy group, $R^4$ is a $C_1$-$C_4$ alkoxy group]. The present invention further relates to (3) a recording material containing a color-forming compound, wherein the recording material contains at least one kind of phenolic compounds represented by formula [1]

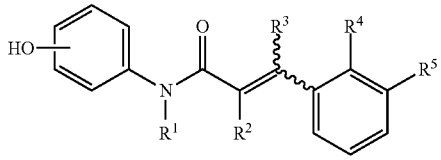
(I)

[wherein $R^1$-$R^3$ each independently represent a hydrogen atom or $C_1$-$C_4$ alkyl group; $R^5$ represents a hydrogen atom, $C_1$-$C_4$ alkyl group or $C_1$-$C_4$ alkoxy group, with the proviso that when $R^5$ is a hydrogen atom, $R^4$ is a $C_1$-$C_4$ alkyl group, when $R^5$ is a $C_1$-$C_4$ alkyl group, $R^4$ is a hydrogen atom, and when $R^5$ is a $C_1$-$C_4$ alkoxy group, $R^4$ is a $C_1$-$C_4$ alkoxy group]; and (4) the recording material containing a color-forming compound according to (3), wherein the recording material contains at least one kind of phenolic compounds represented by formula (II)

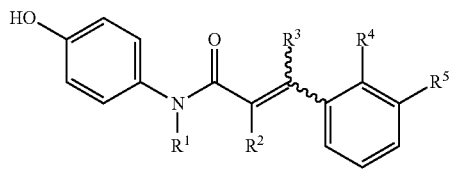
(II)

[wherein $R^1$-$R^3$ represent a hydrogen atom; $R^5$ represents a hydrogen atom, $C_1$-$C_4$ alkyl group or $C_1$-$C_4$ alkoxy group, with the proviso that when $R^5$ is a hydrogen atom, $R^4$ is a $C_1$-$C_4$ alkyl group, when $R^5$ is a $C_1$-$C_4$ alkyl group, $R^4$ is a hydrogen atom, and when $R^5$ is a $C_1$-$C_4$ alkoxy group, $R^4$ is a $C_1$-$C_4$ alkoxy group].

Effect of the Invention

According to the present invention, a recording material can be obtained which has a nonconventional storage property for both of the background and the image and especially which is practically quite superior in any of light resistance of the background, and light, moisture and heat resistance of the image.

MODE OF CARRYING OUT THE INVENTION

Recording Material

A recording material of the present invention can be used for any purpose, for example, for thermal recording materials or pressure sensitive copying materials, as long as the recording material contains a color-forming compound and at least one kind of phenolic compounds represented by formula [I]

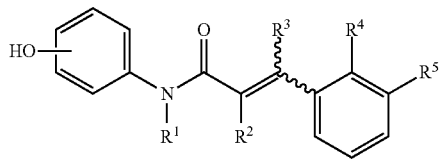
(I)

[wherein $R^1$-$R^3$ each independently represent a hydrogen atom or $C_1$-$C_4$ alkyl group; $R^5$ represents a hydrogen atom, $C_1$-$C_4$ alkyl group or $C_1$-$C_4$ alkoxy group, with the proviso that when $R^5$ is a hydrogen atom, $R^4$ is a $C_1$-$C_4$ alkyl group, when $R^5$ is a $C_1$-$C_4$ alkyl group, $R^4$ is a hydrogen atom, and when $R^5$ is a $C_1$-$C_4$ alkoxy group, $R^4$ is a $C_1$-$C_4$ alkoxy group].

Particularly preferred is a recording material using a phenolic compound represented by formula (II), in which the substitution position of a phenolic hydroxy group is limited to the 4-position, (II)

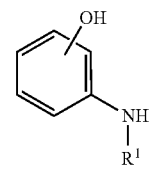

[wherein $R^1$-$R^3$ represent a hydrogen atom; $R^5$ represents a hydrogen atom, $C_1$-$C_4$ alkyl group or $C_1$-$C_4$ alkoxy group, with the proviso that when $R^5$ is a hydrogen atom, $R^4$ is a $C_1$-$C_4$ alkyl group, when $R^5$ is a $C_1$-$C_4$ alkyl group, $R^4$ is a hydrogen atom, and when $R^5$ is a $C_1$-$C_4$ alkoxy group, $R^4$ is a $C_1$-$C_4$ alkoxy group].

(Method for Producing a Phenolic Compound Represented by Formula (I))

A compound represented by formula (I) to be used in the present invention can be obtained by reacting a compound represented by formula (III)

(III)

[wherein $R^1$ has the same meaning as defined above] and a compound represented by formula (IV)

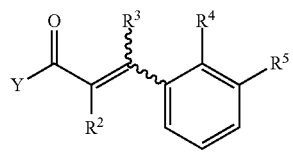
(IV)

[wherein $R^2$-$R^5$ have the same meaning as defined above; and Y represents a halogen atom such as a chlorine atom and bromine atom] in an organic solvent such as acetonitrile and in the presence of a base such as pyridine.

A compound of the present invention represented by formula (I) has geometric isomers as shown below. There are cases where either type of geometric isomer is obtained or where a mixture of geometric isomers is obtained depending on the reaction conditions and purification methods. All of these geometric isomers are encompassed in the scope of the present invention.

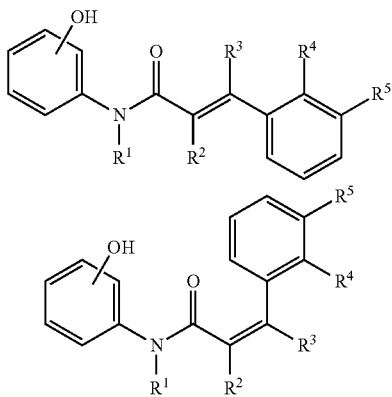

(Phenolic Compound Represented by Formula (I))

A phenolic compound represented by formula (I) is explained below.

In formula (I), $R^1$-$R^3$ are each independently exemplified by a hydrogen atom, and a $C_1$-$C_4$ alkyl group such as a methyl group, ethyl group, n-propyl group, isopropyl group, n-butyl group, sec-butyl group and t-butyl group. Especially preferred is a case where all of $R^1$-$R^3$ are hydrogen atoms.

Examples of $R^4$ include a hydrogen atom; a $C_1$-$C_4$ alkyl group such as a methyl group, ethyl group, n-propyl group, isopropyl group, n-butyl group, sec-butyl group and t-butyl group; and a $C_1$-$C_4$ alkoxy group such as a methoxy group, ethoxy group, n-propoxy group, isopropoxy group, n-butoxy group, sec-butoxy group and t-butoxy group.

However, when $R^5$ is a hydrogen atom, $R^4$ is always a $C_1$-$C_4$ alkyl group; when $R^5$ is an alkyl group, $R^4$ is always a hydrogen atom; and when $R^5$ is an alkoxy group, $R^4$ is always an alkoxy group.

Examples of $R^5$ include a hydrogen atom; a $C_1$-$C_4$ alkyl group such as a methyl group, ethyl group, n-propyl group, isopropyl group, n-butyl group, sec-butyl group and t-butyl group; and a $C_1$-$C_4$ alkoxy group such as a methoxy group, ethoxy group, n-propoxy group, isopropoxy group, n-butoxy group, sec-butoxy group and t-butoxy group.

Representative compounds represented by formula (I) are shown below.

N-(4-hydroxyphenyl)-2-methylcinnamoylamide
N-(4-hydroxyphenyl)-3-methylcinnamoylamide
N-(4-hydroxyphenyl)-2,3-dimethoxycinnamoylamide (Other Components of a Recording Material)

Other than a color-forming compound and a compound represented by formula (I), a recording material of the present invention may further contain as necessary one or more of the following: a known color-developing agent, image stabilizer, sensitizer, filler, dispersant, antioxidant, desensitizer, antiadhesive agent, defoamer, light stabilizer, fluorescent brightener, etc. These are respectively used in an amount of usually within a range of 0.1 to 15 parts by mass, preferably 1 to 10 parts by mass, relative to 1 part by mass of the color-forming compound.

These agents may be contained in the color-forming layer, while they may be contained in any layer such as a protective layer when the recording material consists of a multilayer structure. Especially, when an overcoat layer or undercoat layer is provided on the upper part and/or the bottom part of the color-forming layer, such overcoat layer and undercoat layer may contain an antioxidant, light stabilizer, etc. Further, an antioxidant and a light stabilizer can be contained in these layers in such a manner as being encapsulated in a microcapsule according to need.

Examples of the color-forming compound to be used for a recording material of the present invention include: a leuco dye such as fluoran-based, phthalide-based, lactam-based, triphenylmethane-based, phenothiazine-based and spiropyran-based dyes. The color-forming compound, however, is not limited to these examples and any color-forming compound may be used as long as it forms color when contacted with a color-developing agent which is an acid substance. Further, although it is a matter of course to use these color-forming compounds singularly to produce a recording material of the color formed by the dye used, the color-forming compounds may also be used in combination of two or more kinds thereof. For example, it is possible to produce a recording material that produces a real black by using dyes developing three primary colors (red, blue, green) or black dyes in combination.

Examples of the fluoran-based color-forming compound include 3,3-bis(p-dimethylaminophenyl)-phthalide, 3,3-bis(p-dimethylaminophenyl)-6-dimethylaminophthalide (alias: crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-cyclohexylamino-6-chlorofluoran, 3-dimethylamino-5,7-dimethylfluoran, 3-N-methyl-N-isopropylamino-6-methyl-7-anilinofluoran, 3-N-methyl-N-isobutylamino-6-methyl-7-anilinofluoran, 3-N-methyl-N-isoamylamino-6-methyl-7-anilinofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-(N-p-tolyl-N-ethylamino)-6-methyl-7-anilinofluoran, 3-pyrrolidino-6-methylamino-7-anilinofluoran, 2-{N-(3'-trifluolmethylphenyl)amino}-6-diethylaminofluoran, 2-{3,6-bis(diethylamino)-9-(o-chloroanilino)xanthylic benzoate lactam}, 3-diethylamino-6-methyl-7-(m-trichloromethylanilino)fluoran, 3-diethylamino-7-(o-chloroanilino)fluoran, 3-dibutylamino-7-(o-chloroanilino)fluoran, 3-N-methyl-N-amylamino-6-methyl-7-anilinofluoran, 3-N-methyl-N-cyclohexylamino-6-methyl-7-anilinofluoran, 3-diethylamino-6-methyl-7-anilinofluoran, 3-diethylamino-6-methyl-7-(2',4'-dimethylanilino)fluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-ethyl-N-propylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilinofluoran 3-pyrrolidino-6-methyl-7-anilinofluoran, 3-piperidino-6-methyl-7-anilinofluoran, 3-dimethylamino-7-(m-trifluoromethylanilino)fluoran, 3-dipentylamino-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylaminobenzo[a]fluoran, 3-diethylamino-5-methyl-7-benzylaminofluoran, 3-diethylamino-5-chlorofluoran, 3-diethylamino-6-(N,N'-dibenzylamino)fluoran, 3,6-dimethoxyfluoran, 2,4-dimethyl-6-(4- dimethylaminophenyl)aminofluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-6-methyl-7-(2,4-xylylamino)fluoran, 3-diethylamino-7-(o-fluoroanilino) fluoran, 3-diphenylamino-6-methyl-7-anilinofluoran, benzoylleucomethylene blue, 6'-chloro-8'-methoxy-benzoindolino-spiropyran, 6'-bromo-3'-methoxy-benzoindolino-spiropyran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl) phthalide, 3-(2'-hydroxy-4'-diethylaminophenyl)-3-(2'-methoxy-5'-methyl-phenyl)phthalide, 3-(2'-methoxy-4'-dimethylaminophenyl)-3-(2'-hydroxy-4'-chloro-5'-methylphenyl)phthalide, 3-morpholino-7-(N-propyl-trifluoromethylanilino)fluoran, 3-pyrrolidino-7-trifluoromethylanilinofluoran, 3-diethylamino-5-chloro-7-(N-benzyl-trifluoromethylanilino) fluoran, 3-pyrrolidino-7-(di-p-chlorophenyl)methylaminofluoran, 3-diethylamino-5-chloro-7-(α-phenylethylamino)fluoran, 3-(N-ethyl-p-toluidino)-7-(α-phenylethylamino)fluoran, 3-diethylamino-7-(o-methoxycarbonylphenylamino)fluoran, 3-diethylamino-5-methyl-7-(α-phenylethylamino)fluoran, 3-diethylamino-7-piperidinofluoran, 2-chloro-3-(N-methyl-toluidino)-7-(p-n-butylanilino)fluoran, 3-(N-methyl-N-isopropylamino)-6-methyl-7-anilinofluoran, 3-dibutylamino-6-methyl-7-anilinofluoran, 3-dipentylamino-6-methyl-7-anilinofluoran, 3,6-bis(dimethylamino)fluorenespiro(9,3')-6'-dimethylaminophthalide, 3-(N-benzyl-N-cyclohexylamino)-5,6-benzo-7-α-naphthylamino-4'-bromofluoran, 3-diethylamino-6-chloro-7-anilinofluoran, 3-N-ethyl-N-(2-ethoxypropyl)amino-6-methyl-7-anilinofluoran, 3-N-ethyl-N-tetrahydrofurfurylamino-6-methyl-7-anilinofluoran, 3-diethylamino-6-methyl-7-mesitidino-4',5'-benzofluoran, and 3-(N-ethyl-p-toluidino)-7-(methylphenylamino)fluoran.

Among these color-forming compounds, the followings are preferred: 3,3-bis(p-dimethylaminophenyl)-6-dimethylaminophthalide, 3-cyclohexylamino-6-chlorofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-diethylamino-7-(o-chloroanilino)fluoran, 3-dibutylamino-7-(o-chloroanilino)fluoran, 3-N-methyl-N-cyclohexylamino-6-methyl-7-anilinofluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-7-(o-fluoroanilino) fluoran, 3-diphenylamino-6-methyl-7-anilinofluoran, benzoylleucomethylene blue, 3-dibutylamino-6-methyl-7-anilinofluoran, 3-N-ethyl-N-tetrahydrofurfurylamino-6-methyl-7-anilinofluoran, and 3-(N-ethyl-p-toluidino)-7-(methylphenylamino)fluoran.

The near-infrared absorption dye can be exemplified by 3-[4-[4-(4-anilino)-anilino]anilino]-6-methyl-7-chlorofluoran, 3,3-bis[2-(4-dimethylaminophenyl)-2-(4-methoxyphenyl)vinyl]-4,5,6,7-tetrachlorophthalide, and 3,6,6'-tris(dimethylamino)spiro(fluorene-9,3'-phthalide).

A compound represented by formula (I) of the present invention is suitably used as a color-developing agent mainly for a thermal recording material, and it may be used alone or in combination with a plurality of known color-developing agents at an arbitrary ratio.

Specific examples of other color-developing agents include: a bisphenol compound such as bisphenol A, 4,4'-sec-butylidenebisphenol, 4,4'-cyclohexylidenebisphenol, 2,2'-bis(4-hydroxyphenyl)-3,3'-dimethylbutane, 2,2'-dihydroxydiphenyl, pentamethylene-bis(4-hydroxybenzoate), 2,2-dimethyl-3,3-di(4-hydroxyphenyl)pentane, 2,2-di(4-hydroxyphenyl)hexane, 2,2-bis(4-hydroxyphenyl)propane, 2,2-bis(4-hydroxyphenyl)butane, 2,2-bis(4-hydroxy-3-methylphenyl)propane, 4,4'-(1-phenylethylidene)bisphenol, 4,4'-ethylidenebisphenol, (hydroxyphenyl)methylphenol, 2,2'-bis(4-hydroxy-3-phenyl-phenyl)propane, 4,4'-(1,3-phenylenediisopropylidene)bisphenol, 4,4'-(1,4-phenylenediisopropylidene)bisphenol, and 2,2-bis(4-hydroxyphenyl)butyl acetate; a sulfur-containing bisphenol compound such as 4,4'-dihydroxydiphenylthioether, 1,7-di(4-hydroxyphenylthio)-3,5-dioxaheptane, 2,2'-bis(4-hydroxyphenylthio)diethylether, and 4,4'-dihydroxy-3,3'-dimethyldiphenylthioether; 4-hydroxybenzoic acid esters such as 4-hydroxybenzoic acid benzyl, 4-hydroxybenzoic acid ethyl, 4-hydroxybenzoic acid propyl, 4-hydroxybenzoic acid isopropyl, 4-hydroxybenzoic acid butyl, 4-hydroxybenzoic acid isobutyl, 4-hydroxybenzoic acid chlorobenzyl, 4-hydroxybenzoic acid methylbenzyl and 4-hydroxybenzoic acid diphenylmethyl; a benzoic acid metal salt such as zinc benzoate and zinc 4-nitrobenzoate; salicylic acids such as 4-[2-(4-methoxyphenyloxy)ethyloxy]salicylate; a salicylate metal salt such as zinc salicylate, and zinc-bis[4-(octyloxycarbonylamino)-2-hydroxybenzoate]; hydroxysulfones such as 4,4'-dihydroxydiphenylsulfone, 2,4'-dihydroxydiphenylsulfone, 4-hydroxy-4'-methyldiphenylsulfone, 4-hydroxy-4'-isopropoxydiphenylsulfone, 4-hydroxy-4'-butoxydiphenylsulfone, 4,4'-dihydroxy-3,3'-diallyldiphenylsulfone, 3,4-dihydroxy-4'-methyldiphenylsulfone, 4,4'-dihydroxy-3,3',5,5'-tetrabromodiphenylsulfone, 4-allyloxy-4'-hydroxydiphenylsulfone, 2-(4-hydroxyphenylsulfonyl) phenol, 4,4'-sulfonylbis[2-(2-propenyl)]phenol, 4-[{4-(propoxy)phenyl}sulfonyl]phenol, 4-[{4-(allyloxy)phenyl}sulfonyl]phenol, 4-[{4-(benzyloxy)phenyl}sulfonyl]phenol, and 2,4-bis(phenylsulfonyl)-5-methyl-phenol; multivalent metal salts of hydroxysulfones such as 4-phenylsulfonylphenoxy zinc, 4-phenylsulfonylphenoxy magnesium, 4-phenylsulfonylphenoxy aluminum and 4-phenylsulfonylphenoxy titanium; 4-hydroxyphthalic acid diesters such as dimethyl 4-hydroxyphthalate; dicyclohexyl 4-hydroxyphthalate, and diphenyl 4-hydroxyphthalate; hydroxy naphthalene acid esters such as 2-hydroxy-6-carboxynaphthalene; trihalomethylsulfones such as tribromomethylphenylsulfones; 4,4'-bis(p-toluenesulfonylaminocarbonylamino) diphenylmethane; sulfonylureas such as N-(4-methylphenylsulfonyl)-N'-(3-(4-methylphenylsulfonyloxy)phenyl)urea; hydroxyacetophenone; p-phenylphenol, 4-hydroxyphenylacetic acid benzyl, p-benzylphenol, hydroquinonemonobenzyl ether, 2,4-dihydroxy-2'-methoxybenzanilide; tetracyanoquinodimethanes; N-(2-hydroxyphenyl)-2-[(4-hydroxyphenyl)thio]acetamide; N-(4-hydroxyphenyl)-2-[(4-hydroxyphenyl)thio]acetamide; 4-hydroxybenzenesulfonanilide; 4'-hydroxy-4-methylbenzenesulfonanilide; 4,4'-bis(4-methyl-3-phenoxycarbonyl)aminophenylureide)) diphenylsulfone; 3-(3-phenylureide)benzenesulfonanilide;

octadecyl phosphate; dodecyl phosphate; a diphenylsulfone cross-linking compound represented by the following formula; and a mixture thereof.

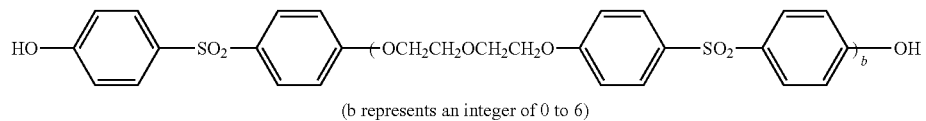

(b represents an integer of 0 to 6)

Preferably exemplified among these are 4-hydroxy-4'-isopropoxydiphenylsulfone, a diphenylsulfone cross-linking compound, and a mixture thereof.

Examples of the image storage stabilizer include epoxy group-containing diphenylsulfones such as 4-benzyloxy-4'-(2-methylglycidyloxy)-diphenylsulfone and 4,4'-diglycidyloxydiphenylsulfone; 1,4-diglycidyloxybenzene, 4-[α-(hydroxymethyl)benzyloxy]-4'-hydroxydiphenylsulfone, 2-propanol derivative, salicylic acid derivative, metal salt (especially zinc salt) of oxynaphthoic acid derivative, metal salt of 2,2-methylenebis(4,6-t-butylphenyl)phosphate, other water-insoluble zinc compounds, 2,2-bis(4'-hydroxy-3',5'-dibromophenyl)propane and 4,4'-sulfonylbis(2,6-dibromophenol).

Examples of the sensitizer include a higher fatty acid amide such as stearic acid amide; benzamide, stearic acid anilide, acetoacetanilide, thioacetanilide; phthalate diesters such as dimethyl phthalate, dibenzyl isophthalate, dimethyl isophthalate, dimethyl terephthalate, diethyl isophthalate, diphenyl isophthalate and dibenzyl terephthalate; dibenzyl oxalate, di(4-methylbenzyl)oxalate, di(4-chlorobenzyl)oxalate, bis(t-butylphenol)s; diethers of 4,4'-dihydroxydiphenylsulfone such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone and 4,4'-dihexyloxydiphenylsulfone; diethers of 2,4'-dihydroxydiphenylsulfone such as 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-diisobutoxydiphenylsulfone, 2,4'-dipentyloxydiphenylsulfone and 2,4'-dihexyloxydiphenylsulfone; 1,2-bis(phenoxy)ethane, 1,2-bis(4-methylphenoxy)ethane, 1,2-bis(3-methylphenoxy)ethane, 1,2-bis(phenoxymethyl)benzene, 2-naphthol benzyl ether, diphenylamine, carbazole, 2,3-di-m-tolylbutane, 4-benzylbiphenyl, 4,4'-dimethylbiphenyl, m-terphenyl, di-β-naphthylphenylenediamine, 1-hydroxy-naphthoic acid phenyl, 2-naphthylbenzyl ether, 4-methylphenyl-biphenylether, 1,2-bis(3,4-dimethylphenyl)ethane, 2,3,5,6-tetramethyl-4'-methyldiphenylmethane, 1,2-bis(phenoxymethyl)benzene, acrylic acid amide, diphenylsulfone, acetylbiphenyl(4'-phenylacetophenone), carbonic acid diphenyl, and 4-acetylbiphenyl.

Preferably exemplified among these are ethers such as 1,2-bis(3-methylphenoxy)ethane and 2-naphthol benzyl ether, and aromatic hydrocarbons such as m-terphenyl, 4-benzylphenyl and di(4-methylbenzyl)oxalate. More preferably exemplified are diphenylsulfone and a derivative thereof, and especially, diethers of 4,4'-dihydroxydiphenylsulfone and diethers of 2,4'-dihydroxydiphenylsulfone are exemplified and the examples include 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexylphenylsulfone, 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-dipentyloxydiphenylsulfone and 2,4'-dihexyloxydiphenylsulfone.

As a filler, silica, clay, kaolin, fired kaolin, talc, satin white, aluminum hydroxide, calcium carbonate, magnesium carbonate, zinc oxide, titanium oxide, barium sulfate, magnesium silicate, aluminum silicate and plastic pigment are exemplified. Preferably exemplified among these are a salt of alkaline earth metal, especially, a carbonate such as calcium carbonate and magnesium carbonate.

Examples of the dispersant include polyvinyl alcohol, polyvinylalcohols of various saponification degrees and polymerization degrees such as acetoacetylated polyvinylalcohol, carboxy-denatured polyvinylalcohol and sulfonic acid-denatured polyvinylalcohol, polysodium acrylate; methylcellulose, carboxymethylcellulose, hydroxyethylcellulose, polyacrylamide, starch, sulfosuccinic acid esters such as dioctylsodium sulfosuccinate, dodecylbenzenesulfonic acid sodium, sodium salt of lauryl alcohol sulfate ester, and a fatty acid salt.

Examples of the antioxidant include 2,2'-methylenebis(4-methyl-6-t-butylphenol), 2,2'-methylenebis(4-ethyl-6-t-butylphenol), 4,4'-propylmethylenebis(3-methyl-6-t-butylphenol), 4,4'-butylidenebis(3-methyl-6-t-butylphenol), 4,4'-thiobis(2-t-butyl-5-methylphenol), 1,1,3-tris(2-methyl-4-hydroxy-5-t-butylphenyl)butane, 1,1,3-tris(2-methyl-4-hydroxy-5-cyclohexylphenyl)butane, 4-{4-[1,1-bis(4-hydroxyphenyl)ethyl]-α,α-dimethylbenzyl}phenol, 1,1,3-tris(2-methyl-4-hydroxy-5-cyclohexylphenyl)butane, 2,2'-methylenebis(6-tert-butyl-4-methylphenol), 2,2'-methylenebis(6-tert-butyl-4-ethylphenol), 4,4'-thiobis(6-tert-butyl-3-methylphenol, 1,3,5-tris[{4-(1,1-dimethylethyl)-3-hydroxy-2,6-dimethylphenyl}methyl]-1,3,5-triazine-2,4,6(1H,3H,5H)-trione, and 1,3,5-tris[{3,5-bis(1,1-dimethylethyl)-4-hydroxyphenyl}meth yl]-1,3,5-triazine-2,4,6(1H,3H,5H)-trione.

Examples of the desensitizer include a fatty higher alcohol, polyethyleneglycol and guanidine derivative, and the examples of the antiadhesive agent include stearic acid, zinc stearate, calcium stearate, carnauba wax, paraffin wax and ester wax.

Examples of the antiadhesive agent include stearic acid, zinc stearate, calcium stearate, carnauba wax, paraffin wax and ester wax.

Examples of the defoamer include those based on higher alcohol, fatty acid ester, oil, silicone, polyether, denatured hydrocarbon and paraffin.

Examples of the light stabilizer include: a salicylic acid-based ultraviolet absorber such as phenylsalicylate, p-t-butylphenylsalicylate and p-octylphenylsalicylate; a benzophenone-based ultraviolet absorber such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4- dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone and bis(2-methoxy-4-hydroxy-5-benzoylphenyl)methane; a benzotriazole-based ultraviolet absorber such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole, 2-(2'-hydroxy-5'-tert-butylphenyl)benzotriazole, 2-(2'-hydroxy-5'-(1",1",3",3"-tetramethylbutyl)phenyl)benzotriazole, 2-[2'-hydroxy-3'-(3",4",5",6"-tetrahydrophthalimidomethyl)-5'-methylphenyl]benzotriazole, 2-(2'-hydroxy-5'-t-octylphenyl)benzotriazole, 2-[2'-hydroxy-3',5'-bis($\alpha,\alpha$-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, 2,2'-methylenebis[4-(1,1,3,3-tetramethylbutyl)-6-(2H-benzotriazole-2-yl)]phenol, and a condensate of polyethyleneglycol and methyl-3-[3-t-butyl-5-(2H-benzotriazole-2-yl)-4-hydroxyphen yl]propionate; a cyanoacrylate-based ultraviolet absorber such as 2'-ethylhexyl-2-cyano-3,3-diphenylacrylate and ethyl-2-cyano-3,3-diphenylacrylate; a hindered amine-based ultraviolet absorber such as bis(2,2,6,6-tetramethyl-4-piperidyl)sebacate, succinic acid-bis(2,2,6,6-tetramethyl-4-piperidyflester, and 2-(3,5-di-t-butyl)malonic acid-bis(1,2,2,6,6-pentamethyl-4-piperidyl)ester; and 1,8-dihydroxy-2-acetyl-3-methyl-6-methoxynaphthalene.

Examples of the fluorescent brightener include 4,4'-bis[2-anilino-4-(hydroxyethyl)amino-1,3,5-triazinyl-6-amino]stilbene-2,2'-disulfonic acid=disodium salt, 4,4'-bis[2-anilino-4-bis(hydroxyethyl)amino-1,3,5-triazinyl-6-amino]stilbene-2,2'-disulfonic acid=disodium salt, 4,4'-bis[2-anilino-4-bis(hydroxypropyl)amino-1,3,5-triazinyl-6-amino]stilbene-2,2'-disulfonic acid=disodium salt, 4,4'-bis[2-methoxy-4-(2-hydroxyethyl)amino-1,3,5-triazinyl-6-amino]stilbene-2,2'-disulfonic acid=disodium salt, 4,4'-bis[2-methoxy-4-(2-hydroxypropyl)amino-1,3,5-triazinyl-6-amino]stilbene-2,2'-disulfonic acid=disodium salt, 4,4'-bis[2-m-sulfoanilino-4-bis(hydroxyethyl)amino-1,3,5-triazinyl-6-amino]stilbene-2,2'-disulfonic acid=disodium salt, 4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid=tetrasodium salt, 4,4'-bis[2-p-sulfoanilino-4-bis(hydroxyethyl)amino-1,3,5-triazinyl-6-amino]stilbene-2,2'-disulfonic acid=tetrasodium salt, 4,4'-bis[2-(2,5-disulfoanilino)-4-phenoxyamino-1,3,5-triazinyl-6-amino]stilbene-2,2'-disulfonic acid=hexasodium salt, 4,4'-bis[2-(2,5-disulfoanilino)-4-(p-methoxycarbonylphenoxy)amino-1,3,5-triazinyl-6-amino]stilbene-2,2'-disulfonic acid=hexasodium salt, 4,4'-bis[2-(p-sulfophenoxy)-4-bis(hydroxyethyl)amino-1,3,5-triazinyl-6-amino]stilbene-2,2'-disulfonic acid=hexasodium salt, 4,4'-bis[2-(2,5-disulfoanilino)-4-formalinylamino-1,3,5-triazinyl-6-amino]stilbene-2,2'-disulfonic acid=hexasodium salt and 4,4'-bis[2-(2,5-disulfoanilino)-4-bis(hydroxyethyl)amino-1,3,5-triazinyl-6-amino]stilbene-2,2'-disulfonic acid=hexasodium salt.

(Method for Producing a Recording Material)

The present invention may be used as a thermal recording paper in a similar manner to known using methods. For example, a thermal recording paper can be produced as follows. Suspension solutions are mixed and applied onto a support, such as a paper, and dried, wherein the suspension solutions are prepared by respectively dispersing microparticles of a compound of the present invention and microparticles of a color-forming compound in the aqueous solutions comprising a water-soluble binder such as polyvinylalcohol and cellulose.

The ratio of a compound represented by formula (I) to be used relative to a color-forming compound is usually 0.01 to 10 parts by mass, preferably 1 to 10 parts by mass, and more preferably 1.5 to 5 parts by mass relative to 1 part by mass of the color-forming compound.

When using a compound of the present invention for a pressure sensitive copying paper, the pressure sensitive copying paper can be produced in a similar manner to when using a known color-developing agent or sensitizer. For example, a color-forming compound which has been microencapsulated by a known method is dispersed with an appropriate dispersant and applied onto a paper to prepare a sheet of color-forming agent. Also, a dispersion solution of a color-developing agent is applied onto a paper to prepare a sheet of color-developing agent. In doing so, when a compound of the present invention is used as an image storage stabilizer, the compound may be used by being dispersed in a dispersion solution for either a sheet of color-forming agent or a sheet of color-developing agent. Both sheets thus prepared are combined to prepare a pressure sensitive copying paper. A pressure sensitive copying paper may be either an unit or a so-called self content paper: wherein the unit is consisting of a upper paper which is applied with and carries on its undersurface the microcapsules encapsulating an organic solvent solution of a color-forming compound and a lower paper which is applied with and carries on its top surface a color-developing agent (acid substance); and wherein the self content paper is applied with microcapsules and a color-developing agent on the same paper surface.

In such case as above, a color-developing agent used and a color-developing agent used by being admixed with a compound of the present invention may be those conventionally known and the examples include: an inorganic acid substance such as an acid earth, activated earth, attapulgite, bentonite, colloidal silica, aluminum silicate, magnesium silicate, zinc silicate, tin silicate, fired kaolin and talc; aliphatic carboxylic acid such as oxalic acid, maleic acid, tartaric acid, citric acid, succinic acid and stearic acid; aromatic carboxylic acid such as benzoic acid, p-t-butylbenzoic acid, phthalic acid, gallic acid, salicylic acid, 3-isopropylsalicylic acid, 3-phenylsalicylic acid, 3-cyclohexylsalicylic acid, 3-5-di-t-butylsalicylic acid, 3-methyl-5-benzylsalicylic acid, 3-phenyl-5-(2,2-dimethylbenzyl)salicylic acid, 3,5-di-(2-methylbenzyl)salicylic acid and 2-hydroxy-1-benzyl-3-naphthoic acid, and a metallic salt such as zinc, magnesium, aluminum and titanium of these aromatic carboxylic acids; a color-developing agent based on phenolic resin such as p-phenylphenol-formalin resin and p-butylphenol-acetylene resin, and a mixture of such phenolic resin-based color-developing agent and the above-mentioned metallic salt of an aromatic carboxylic acid.

A support used in the present invention may be a conventionally known paper, synthetic paper, film, plastic film, foamed plastic film, non-woven fabric, recycled paper such as waste paper pulp. A mixture of these may also be used as a support.

EXAMPLES

A recording material of the present invention is explained in detail below with reference to the Examples, but the present invention shall not necessarily be limited only to these exemplifications.

Example 1

Synthesis of a Phenolic Compound:
N-(4-hydroxyphenyl)-2,3-dimethoxycinnamoylamide To a 500 mL four-neck recovery flask equipped with an agitator and a thermometer, dichloromethane (200 mL) and 41.6 g (0.20 mol) of 2,3-dimethoxycinnamic acid were added. Thereto were added 27.9 g (0.22 mol) of oxalyl chloride and DMF (10 drops) and the resultant mixture was reacted for 4 hours at room temperature. The solvent in the obtained solution was distilled and the corresponding acid chloride was obtained. Subsequently, to a 1 L four-neck recovery flask equipped with an agitator and a thermometer containing a mixture solvent of acetone (600 mL) and distilled water (200 mL), 24.0 g (0.22 mol) of 4-aminophenol and 18.5 g (0.22 mol) of sodium hydrogen carbonate were dissolved. Thereto, acid chloride dissolved in dichloromethane (120 mL) was added dropwise in an ice bath, and the resultant mixture was reacted for 18 hours. The crystal obtained after distilling the solvent was separated by filtration, dried under reduced pressure at 70° C., and a crystal yield of 28.3 g was obtained.

Melting point 208-210° C.
$^1$H-NMR (DMSO, δ ppm): 3.80 (s, 3H), 3.82 (s, 3H), 6.80 (td, 1H), 6.87-6.95 (m, 2H), 7.00 (d, 1H), 7.06 (d, 1H), 7.18 (dd, 1H), 7.26 (d, 1H), 7.50 (d, 1H), 7.95 (d, 1H), 9.35 (brs, 1H)

Example 2

Synthesis of a Phenolic Compound:
N-(4-hydroxyphenyl)-3-methylcinnamoylamide

To a 500 mL four-neck recovery flask equipped with an agitator and a thermometer, dichloromethane (200 mL) and 32.4 g (0.20 mol) of 3-methylcinnamic acid were added. Thereto were added 27.9 g (0.22 mol) of oxalyl chloride and DMF (10 drops) and the resultant mixture was reacted for 4 hours at room temperature. The solvent in the obtained solution was distilled and the corresponding acid chloride was obtained. Subsequently, to a 1 L four-neck recovery flask equipped with an agitator and a thermometer containing a mixture solvent of acetone (600 mL) and distilled water (200 mL), 24.0 g (0.22 mol) of 4-aminophenol and 18.5 g (0.22 mol) of sodium hydrogen carbonate were dissolved. Thereto, acid chloride dissolved in dichloromethane (120 mL) was added dropwise in an ice bath, and the resultant mixture was reacted for 18 hours. The crystal obtained after distilling the solvent was separated by filtration, dried under reduced pressure at 70° C., and a crystal yield of 14.4 g was obtained.

Melting point 207-208° C.
$^1$H-NMR (DMSO, δ ppm): 3.39 (s, 3H), 6.72 (d, 2H), 6.78 (d, 1H), 7.20 (d, 1H), 7.32 (t, 1H), 7.38-7.41 (m, 2H), 7.48 (dd, 3H), 9.25 (brs, 1H)

Example 3

Synthesis of a Phenolic Compound:
N-(4-hydroxyphenyl)-2-methylcinnamoylamide

To a 500 mL four-neck recovery flask equipped with an agitator and a thermometer, dichloromethane (200 mL) and 9.7 g (0.06 mol) of 2-methylcinnamic acid were added. Thereto were added 9.2 g (0.07 mol) of oxalyl chloride and DMF (10 drops) and the resultant mixture was reacted for 4 hours at room temperature. The solvent in the obtained solution was distilled and the corresponding acid chloride was obtained. Subsequently, to a 1 L four-neck recovery flask equipped with an agitator and a thermometer containing a mixture solvent of acetone (120 mL) and distilled water (30 mL), 7.2 g (0.07 mol) of 4-aminophenol and 5.6 g (0.07 mol) of sodium hydrogen carbonate were dissolved. Thereto, acid chloride dissolved in dichloromethane (120 mL) was added dropwise in an ice bath, and the resultant mixture was reacted for 18 hours. The crystal obtained after distilling the solvent was separated by filtration, dried under reduced pressure at 70° C., and a crystal yield of 5.0 g was obtained.

Melting point 192-194° C.
$^1$H-NMR (DMSO, δ ppm): 2.41 (s, 3H), 6.71 (d, 1H), 6.75 (d, 2H), 7.20-7.35 (m, 3H) 7.52 (d, 2H), 7.58 (m, 1H), 7.77 (d, 1H), 9.25 (brs, 1H)

Example 4

| (Production of a thermal recording paper) | |
| --- | --- |
| Dispersion solution of a dye (solution A) | |
| 3-Di-n-butylamino-6-methyl-7-anilinofluoran | 16 parts |
| Aqueous solution of 10% polyvinylalcohol | 84 parts |
| Dispersion solution of a color-developing agent (solution B) | |
| Compound of Example 1 | 16 parts |
| Aqueous solution of 10% polyvinylalcohol | 84 parts |
| Dispersion solution of a filler (solution C) | |
| Calcium carbonate | 27.8 parts |
| Aqueous solution of 10% polyvinylalcohol | 26.2 parts |
| Water | 71 parts |

("parts" denotes "parts by mass")

First, mixtures of solutions A to C consisting of respective components were respectively ground well in a sand grinder to prepare the dispersion solutions of solutions A to C consisting of the respective components. A coating solution was prepared by mixing 1 part by mass of solution A, 2 parts by mass of solution B and 4 parts by mass of solution C. This coating solution was applied and dried on a white paper using a wire rod (Wire bar No. 12, Webster), followed by a calendar treatment to produce a thermal recording paper (coating solution: about 5.5 g/m$^2$ in terms of dry mass).

Example 5

A thermal paper is produced similarly to the method of Example 4, except that the compound of Example 2 was used in place of the compound of Example 1 for the dispersion solution of a color-developing agent (Solution B) in Example 4.

Example 6

A thermal paper is produced similarly to the method of Example 4, except that the compound of Example 3 was used in place of the compound of Example 1 for the dispersion solution of a color-developing agent (Solution B) in Example 4.

Comparative Example 1

A thermal paper is produced similarly to the method of Example 4, except that (E)-N-(2-hydroxyphenyl)cinnamoylamide (the compound of Example 1 in Japanese Unexamined Patent Application Publication No. 2003-305959) was used in place of the compound of Example 1 for the dispersion solution of a color-developing agent (Solution B) in Example 4.

Comparative Example 2

A thermal paper is produced similarly to the method of Example 4, except that (E)-N-(3-hydroxyphenyl)cinnamoylamide (the compound of Example 2 in Japanese Unexamined Patent Application Publication No. 2003-305959) was used in place of the compound of Example 1 for the dispersion solution of a color-developing agent (Solution B) in Example 4.

Comparative Example 3

A thermal paper is produced similarly to the method of Example 4, except that (E)-N-(4-hydroxyphenyl)cinnamoylamide (the compound of Example 3 in Japanese Unexamined Patent Application Publication No. 2003-305959) was used in place of the compound of Example 1 for the dispersion solution of a color-developing agent (Solution B) in Example 4.

(Test 1)
(Thermal Evaluation Test—Background Light Resistance Test)

A part of each of the thermal recording papers produced in Examples 4-6 and Comparative Examples 1-3 was cut off and subjected to a light resistance test using a light resistance test device (UV Long-Life Fade Meter U48, Suga Test Instruments Co., Ltd.). Then, the background density after 24 hours was determined using a Macbeth Reflection Densitometer (filter used: #47). The results are shown in Table 1.

(Test 2)
(Thermal Evaluation Test—Moisture and Heat Resistance of the Image)

A part of each of the thermal recording papers produced in Examples 4-6 and Comparative Examples 1-3 was cut off and colored under the condition of 0.72 mj per dot using a thermal printing tester (model name: TH-PMH, Ohkura Electric Co., Ltd.). A moisture and heat resistance test was conducted for the colored image with a moisture and heat resistance test device (Constant Low Temperature Humidity Chamber THNO50FA, Advantec Toyo Kaisha, Ltd.). Then, the colored image density after 24 hours was determined using a Macbeth Reflection Densitometer (filter used: #106) to calculate the residual ratio based on the initial state. The results are shown in Table 1.

(Test 3)
(Thermal Evaluation Test—Light Resistance of the Image)

A part of each of the thermal recording papers produced in Examples 4-6 and Comparative Examples 1-3 was cut off and colored under the condition of 0.72 mj per dot using a thermal printing tester (model name: TH-PMH, Ohkura Electric Co., Ltd.). A light resistance test was conducted for the colored image using a light resistance test device (UV Long-Life Fade Meter U48, Suga Test Instruments Co., Ltd.). Then, the colored image density after 24 hours was determined using a Macbeth Reflection Densitometer (filter used: #106) to calculate the residual ratio based on the initial state. The results are shown in Table 1.

TABLE 1

| | Test 1 Background light resistance | | Test 2 Image moisture and heat resistance | | Test 3 Image light resistance | |
|---|---|---|---|---|---|---|
| Example 4 | 0.19 | ◎ | 97% | ◎ | 71% | ◎ |
| Example 5 | 0.19 | ◎ | 100% | ◎ | 67% | ◎ |
| Example 6 | 0.20 | ◎ | 94% | ◎ | 77% | ◎ |
| Comparative Example 1 | 0.26 | Δ | 37% | Δ | 61% | ◎ |
| Comparative Example 2 | 0.25 | Δ | 75% | ◯ | 54% | Δ |
| Comparative Example 3 | 0.24 | Δ | 98% | ◎ | 63% | ◎ |

◎: Practically good
◯: Somewhat inferior but practically no problem
Δ: Practically not good

The invention claimed is:

1. A phenolic compound represented by formula (II)

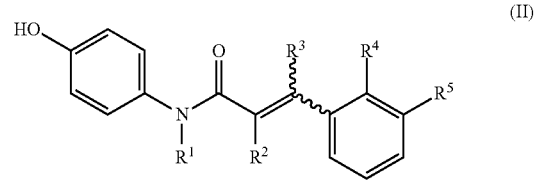

(II)

wherein $R^1$-$R^3$ represent a hydrogen atom; when $R^5$ is a hydrogen atom, $R^4$ is a $C_1$-$C_4$ alkyl group; when $R^5$ is a $C_1$-$C_4$ alkyl group, $R^4$ is a hydrogen atom; and when $R^5$ is a $C_1$-$C_4$ alkoxy group, $R^4$ is a $C_1$-$C_4$ alkoxy group.

2. A recording material containing a color-forming compound according to claim 1, wherein the recording material contains at least one of phenolic compounds represented by formula (II)

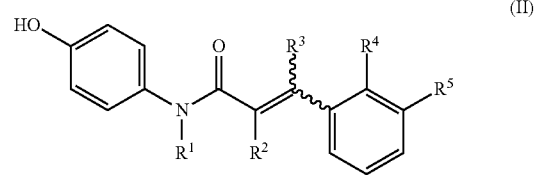

(II)

wherein $R^1$-$R^3$ represent a hydrogen atom; when $R^5$ is a hydrogen atom, $R^4$ is a $C_1$-$C_4$ alkyl group; when $R^5$ is a $C_1$-$C_4$ alkyl group, $R^4$ is a hydrogen atom; and when $R^5$ is a $C_1$-$C_4$ alkoxy group, $R^4$ is a $C_1$-$C_4$ alkoxy group.

* * * * *